US005877176A

United States Patent [19]
Gross

[11] Patent Number: 5,877,176
[45] Date of Patent: Mar. 2, 1999

[54] BLOCKING INDUCTION OF TETRAHYDROBIOPTERIN TO BLOCK INDUCTION OF NITRIC OXIDE SYNTHESIS

[75] Inventor: Steven S. Gross, New York, N.Y.

[73] Assignee: Cornell Research Foundation, Inc., Ithaca, N.Y.

[21] Appl. No.: 151,889

[22] Filed: Nov. 15, 1993

Related U.S. Application Data

[63] Continuation-in-part of Ser. No. 63,067, May 20, 1993, which is a continuation of Ser. No. 813,507, Dec. 26, 1991, abandoned.

[51] Int. Cl.$^6$ .................. A61K 31/495; A61K 31/405; A61K 31/195
[52] U.S. Cl. .................. 514/253; 514/415; 514/567
[58] Field of Search .................. 514/253, 415, 514/567

[56] References Cited

U.S. PATENT DOCUMENTS

| | | | |
|---|---|---|---|
| 3,557,106 | 1/1971 | Roch | 544/260 X |
| 4,282,217 | 8/1981 | Baglioni et al. | 424/240 |
| 4,670,438 | 6/1987 | Austel et al. | 514/249 |
| 4,701,455 | 10/1987 | Nichol et al. | 514/249 |
| 4,734,438 | 3/1988 | Macri | 514/653 |
| 5,002,944 | 3/1991 | Spada et al. | 514/221 |
| 5,028,627 | 7/1991 | Kilbourn et al. | 514/565 |
| 5,059,712 | 10/1991 | Griffith | 562/560 |
| 5,132,453 | 7/1992 | Griffith | 562/560 |
| 5,158,883 | 10/1992 | Griffith | 435/240.2 |
| 5,196,195 | 3/1993 | Griffith | 424/94.6 |
| 5,216,025 | 6/1993 | Gross et al. | 514/565 |
| 5,273,875 | 12/1993 | Griffith | 435/1 |
| 5,281,627 | 1/1994 | Griffith | 514/564 |
| 5,298,506 | 3/1994 | Stamler et al. | 514/226.2 |
| 5,419,901 | 5/1995 | Griffith | 424/94.1 |
| 5,449,688 | 9/1995 | Wahl et al. | 514/546 |

FOREIGN PATENT DOCUMENTS

| | | | |
|---|---|---|---|
| 446699 | 9/1991 | European Pat. Off. | A61K 31/408 |
| WO8404040 | 10/1984 | WIPO | A61L 31/495 |
| PCT/US90/05199 | 9/1990 | WIPO | |

OTHER PUBLICATIONS

Gray, G.A., et al. Br. J. Pharmacol., 103, 1218–1224 (May 1991).
Aisaka, K., et al, Biochem. Biophys. Res. Commun. 163, No. 2, 710–717 (Sep. 15, 1989).
Jolou–Schaeffer, G., et al, Am. J. Physiol. 259, H1038–H1043, Oct. 1990.
Book of Abstracts, Second International Meeting Biology of Nitric Oxide, cover page, meeting schedule page, abstract headed.
Synthesis of Tetrahydrobiopterin is a Requirement for Induction of Nitric Oxide Synthesis by LPS/Interferon in Vascular Smooth Muscle (Steven S. Gross and Roberto Levi).
Gross, S., et al, FASEB Journal 6, A 1509, 1992.
Gross, S., J. Vasc. Res., 29, 125–126, Abstract 147, 1992.
Galivan et al 1987 106CA:27532u.
Krumdieck et al 1991 115CA:150382h.
Zhang et al 1991 114CA:55456P.
Rees, D.D., et al, Chem. Abstr. 110: 112347q (1989).
Salvemini, D., et al, Chem. Abstr. 115: 204139e (1991).
Rees, D.D., et al, Br. J. Pharmacol., 101, 746–752 (1992).
Stuehr, D.J., et al, Advances in Enzymology 65, 287–346 (1992).
Selye, H., Proc. Soc. Exper. Biol. & Med. 82, 328–333 (1953).
Selye, H., J. Am. Med. Assoc., 152, 1207–1213 (1953).
Nichol, C., et al, Ann. Rev. Biochem. 54, 729–764 (1985).
Tayeh, M.A., et al, J. Biol. Chem., 264, No. 33, 19654–19658 (1989).
Werner–Felmayer, G., et al, J. Exp. Med., 172, 1599–1607 (1990).
Moncada, S., et al, Pharmacological Reviews 43(2):109–142 (1991).
Gross, S.S., et al, J. Biol. Chem. 267, 25722–25729 (Dec. 1992).
Kilbourn, R.G., et al, Biochem. Biophys. Res. Commun. 172, 1132–1138 (Nov. 1990).
Kilbourn, R.G., et al, J. Natl. Cancer Inst. 84, 827–831 (Jun. 1992).
Kwon, N.S., et al, Chem. Abstr. 111: 230525q (1989).
Merck Index, 10th Ed., #s 1227 and 7834.
Vallance, P., et al, New Horizons 77–86 (Feb. 1993).
Rees, D.D., et al, Chem. Abstr. 110: 112347q (1989).
Salvemini, D., et al, Chem. Abstr. 115: 204139e (1991).
Selye, H., Proc. Soc. Exper. Biol. & Med. 82, 328–333 (1953).
Selye, H., J. Am. Med. Assoc., 152, 1207–1213 (1953).
Moncada, S., et al, Eur. J. Clin. Invest. 21, 361–374 (1991).
Moncada, S., et al, Cardiovascular Pharm. 17 (suppl. 3), S1–S9 (1991).
Rees, D.D., et al, Nitric oxide from L–arginine: a bioregulatory system, S. Moncada et al eds., Elsevier Science Publishers, BV, 485–487 (1990).

(List continued on next page.)

*Primary Examiner*—Russell Travers

[57] ABSTRACT

Guanosine triphosphate pathway tetrahydrobiopterin synthesis antagonist and/or pterin salvage pathway tetrahydrobiopterin synthesis antagonists are administered to inhibit nitric oxide synthesis from arginine in vascular cells in a subject in need of such inhibition (e.g., for prophylactic or curative effect for endotoxin- or cytokine-induced hypotension or for restoration of vascular contractile sensitivity to pressor agents in the treatment of such hypotension). The tetrahydrobiopterin synthesis antagonist may be administered with $\alpha_1$-adrenergic agonist or with nitric oxide synthase inhibitor. The tetrahydrobiopterin synthesis antagonists are also administered to attenuate inflammation caused by induced nitric oxide production in immune cells. Unwanted counterproductive or side effects can be eliminated or ameliorated by administration additionally of levodopa with or without carbidopa and L-5-hydroxytryptophane.

18 Claims, 9 Drawing Sheets

OTHER PUBLICATIONS

Steuhr, D.J. et al, Synthesis of Nitrogin Oxide from L-Arginine by Macrophage Cytosol: Requirement for Inducible and Constitutive Components, *Biochem. Biophys. Res. Commun.,* (1989) vol. 161, 420–426.

Stuehr, D.J. et al., Activated Murine Macrophages Secrete a Metabolite of Arginine with the Bioactivity of Endothelium–Derived Relaxing Factor and the Chemical Reactivity of Nitric Oxide, *J. Exp. Med.,* (1989) vol. 169, 1011–1020.

Rees, D.D. et al., Role of Endothelium–Derived Nitric Oxide in the Regulation of Blood Pressure, *Proc. Natl. Acad. Sci. U.S.A.,* (1989) vol. 86, 3375–3378.

Aisaka, K. et al., $N^G$–Methylarginine, An Inhibitor of Endothelium–Derived Nitric Oxide Synthesis, is a Potent Pressor Agent in the Guinea Pig: Does Nitric Oxide Regulate Blood Pressure in vivo, *Biochem. Biophys. Res. Commun.* (1989) 160:881–886.

Natanson, C. et al., Endotoxin and Tumor Necrosis Factor Challenges in Dogs Simulate the Cardiovascular Profile of Human Septic Shock, *Journal of Exp. Med.* (1989) 169:823–832.

Schmidt, H. et al., Arginine is a Physiological Precursor of Endothelium–Derived Nitric Oxide, *Eur. J. of Pharmacology* (1988) 154:213–216.

Palmer, R.M.J. et al., L–Arginine is the Physiological Precursor for the Formation of Nitric Oxide in Endothelium–Dependent Relaxation, *Biochem. Biophys. Res. Commun.* (1988) 153:1251–1256.

Sakuma, I. et al., Identification of Arginine as a Precursor of Endothelium–Derived Relaxing Factor, *Proc. Natl. Acad. Sci U.S.A.* (1988) 85:8664–8667.

Palmer, R.M.J. et al., Vascular Endothelial Cells Synthesis Nitric Oxide from Arginine, *Nature,* (1988) vol. 333, 664–666.

Hibbs, J.B. et al., Nitric Oxide: A Cytotoxic Activated Macrophage Effector Molecule, *Biochem. Biophys. Res. Commun.* (1988) 157:87–94.

Marletta, M.A. et al., Macrophage Oxidation of L–Arginine to Nitrite and Nitrate: Nitric Oxide Is an Intermediate, *Biochemistry* (1988) 27:8706–8711.

Palmer, R.M.J. et al., Nitric Oxide Release Accounts for the Biological Activity of Endothelium–Derived Relaxing Factor, *Nature* (1987) 327:524–526.

Steuhr, D.J. et al., Induction of Nitric/Nitrate Synthesis in Murine Macrophages by BCG Infection, Lymphokines, or Interferon–$\gamma$, *J. of Immunology* (1987) 139:518–525.

Iyengar, R. et al., Macrophage Synthesis of Nitrate, Nitrate and N–Nitrosamines: Precursors and Role of the Respiratory Burst, *Proc. Natl. Acad. Sci. U.S.A.* (1987) vol. 84, 6369–6373.

Turan et al., *Acta Chimica Academiae Scientiarum Hungaricae* (1975) 85:327–332.

Kilbourn et al., $N^G$–Methyl–L–Arginine Inhibits Tumor Necrosis Factor–Induced Hypotension: Implications for the Involvement of Nitric Oxide *Proc. Natl. Acad. Sci. U.S.A.* (1990) 87:3629–3632.

Gross, S.S.,et al,Biochem.Biophys.Res.Commun, 178, No. 3, 823–829 (Aug. 15, 1991).

Kaufman, S, et al, J. Biol. Chem., 234, No. 10, 2683–2688 (Oct. 1959).

Kaufman, S., et al, J. Biol. Chem., 242, No. 17, 3934–3943 (Sep. 1967).

Kerler, F., et al, Exp. Cell Res., 189, 151–156 (1990).

Kwon, N.S., et al, J. Biol. Chem., 264, No. 34, 20496–20501 (Dec. 1989).

Milstien, S., et al, Biochem. Biophys. Res. Commun., 128, No. 3, 1099–1107 (May 1985).

Christen et al 112CA:233431N 1990.

Bhattachorya et al 106CA:13424y 1987.

Bhattacharya, S. K., et al, Chemical Abstracts 106:13424y (Jul. 1989).

Ziegler, I., et al, J. Biol. Chem., 265, No. 28, 17026–17030 (Oct. 1990).

Marletta, M.A., "Nitric oxide: biosynthesis and biological significance," name of publication unknown, Elsevier Science Publishers, Ltd. (UK), pp. 448–453 (1989).

Collier, J., et al, Trends in Pharmacological Sciences Including Toxicological Sciences, Elsevier Science Publishers, Ltd., published in UK 1989, frontpage and pp. 428–431.

Rees, D.D., et al, Br. J. Pharmacol., 96, 418–424 (1989).

Werner, E., et al, Biochem. J., 262:861–866 (1989).

Gross, S.S., et al, Biochem. Biophys. Res. Commun. 170, 96–103 (Jul. 1990).

Corbett, J. A., et al, J. Clin. Invest. 90, 2384–2391 (1992).

Corbett, J. A., et al, Proc. Natl. Acad. Sci. USA, 90, 1731–1735 (Mar. 1993).

Ialenti, A., et al, Eur. J. Pharmacol. 211, 177–182 (1992).

Kleeman, R., et al, FEBS, 328, 9–12 (Aug. 1993).

McCartney–Francis, N., et al, J. Exp. Med. 178, 749–754 (1993).

Misko, T. P., et al, Eur. J. Pharmacol. 233, 119–125 (1993).

Corbett, J. A., et al, Proc. Natl. Acad. Sci. USA, 90, 8992–8995 (Oct. 1993).

Corbett, J. A, et al, Biochemistry 32, 13756–13770 (1993).

Kroncke, K.–D., et al, Biochem. Biophys. Res. Commun. 175, 752–758 (1991).

Lukic, M. L., et al, Biochem. Biophys. Res. Commun. 178, 913–920 (1991).

Mulligan, M. S., et al, Proc. Natl. Acad. Sci. USA, 88, 6338–6342 (Jul. 1991).

Mulligan, M. S., et al, Br. J. Pharmacol. 107, 1159–1162 (1992).

Nathan, C. F., et al, Current Opinion in Immunology, 3, 65–7 (1991).

Kilbourn, R.G., et al, Journal of the National Cancer Institute, 84, No. 13, 1008–1016 (Jul. 1, 1992).

BLOCKING INDUCTION OF TETRAHYDROBIOPTERIN TO BLOCK INDUCTION OF NITRIC OXIDE SYNTHESIS

CROSS-REFERENCE TO RELATED APPLICATION

This is a continuation-in-part of U.S. Ser. No. 08/063,067, filed May 20, 1993 which is a continuation of U.S. Ser. No. 07/813,507, filed Dec. 26, 1991 now abandoned.

This invention was made at least in part with Government support under Grants HL46403 from the National Institutes of Health.

TECHNICAL FIELD

This invention is directed to a novel method of inhibiting the induction of nitric oxide formation in biological systems by bacterial endotoxins and cytokines.

BACKGROUND OF THE INVENTION

For several decades nitroglycerin has been administered to humans as a vasodilating agent in the treatment of cardiovascular disease. Recently, it has been shown that nitroglycerin so administered is converted in the body to nitric oxide which is the pharmacologically active metabolite. Still more recently, nitric oxide has been shown to be formed enzymatically from arginine as a normal metabolite which is an important component of endotheliumderived relaxing factors (EDRFs). EDRFs are currently being intensively studied as participating in regulation of blood flow and vascular resistance. In addition to vascular endothelium, macrophages have also been shown to produce nitric oxide in the body which is a component of their cell killing and/or cytostatic function.

It has been established that the enzyme forming nitric oxide from arginine, i.e., nitric oxide synthase, occurs in two distinct types, namely the constitutive forms and an inducible form. Constitutive forms are present in normal endothelial cells, certain neurons and some other tissues. Formation of nitric oxide by the constitutive form in endothelial cells is thought to play a role in normal blood pressure regulation. The inducible form of nitric oxide synthase has been found to be present in activated macrophages and is induced in endothelial cells and vascular cells, for example, by various cytokines and/or microbial products. It is thought that in sepsis or cytokine-induced shock, overproduction of nitric oxide by the inducible form of nitric oxide synthase plays an important role in the observed life-threatening hypotension. Furthermore, it is thought that overproduction of nitric oxide by the inducible form of nitric oxide synthase is a basis for insensitivity to pressor agents such as $\alpha_1$-adrenergic agonists, used in the treatment of septic or cytokine-induced shock in patients. Moreover, it is thought that overproduction of nitric oxide by the inducible form of nitric oxide synthase is involved in inflammation incident to an immune response.

Considerable research effort has been expended to discover inhibitors of nitric oxide synthase activity. Before the work described herein, said research effort has been directed at uncovering arginine antagonists which inhibit nitric oxide synthase activity. A problem with use of the arginine antagonists for this purpose is that the ones uncovered thus far block not only inducible nitric oxide synthase activity but also constitutive nitric oxide synthase activity; and any specificity of inhibition of any particular arginine antagonist for inducible nitric oxide synthase activity is not so high that it is possible to block hypotension-causing, pathological overproduction of nitric oxide (an inducible enzyme-mediated process) to a therapeutically adequate extent (i.e., so that clinically serious hypotension that would normally occur in sepsis or cytokine-induced shock is avoided or so that pressor agent sensitivity is restored), and, at the same time, not block the physiological nitric oxide synthesis which is thought to play a role in neural function and normal blood pressure regulation (constitutive enzyme-mediated processes) and thereby avoid the toxicity (e.g. neuronal toxicity and hypertension) associated with interfering with physiological nitric oxide synthesis.

SUMMARY OF THE INVENTIONS

The inventions herein do not rely primarily on arginine antagonists but rather use a novel approach to selectively block the induction of nitric oxide synthesis by cytokines and/or microbial products (e.g., bacterial endotoxins) with a reduced inhibitory effect on physiological (constitutive enzyme-mediated) nitric oxide production.

The inventions herein draw on the recent discovery that tetrahydrobiopterin is a cofactor in the induction of nitric oxide synthesis (Kwon, N. C., et al, J. Biol. Chem. 264:20496–20501, 1989, and Tayeh, M. A., et al J. Biol Chem. 264:19654–19658, 1989).

The inventions herein also draw on the discovery that cytokines, e.g., interferons including interferon-gamma, tumor necrosis factor, interleukin-1 and interleukin-2, have been found to markedly increase tetrahydrobiopterin levels in various cells (Werner, E., et al, Biochem. J 262:861–866, 1989; Kerler, F., et al, Experimental Cell Research 189, 151–156, 1990; Ziegler, I., et al, The Journal of Biological Chemistry, 265, No. 28, 17026–17030, Oct. 5, 1990), the discovery in the course of the inventions herein that tetrahydrobiopterin synthesis is induced by bacterial endotoxins, the discoveries that tetrahydrobiopterin synthesis occurs via a guanosine triphosphate pathway and via a pterin salvage pathway (Nichol, C., et al, Ann. Rev. Biochem. 54, 729–764, 1985; Milstien, S., et al, Biochem. and Biophys. Res. Comm., 128, No. 3, 1099–1107, 1985; Kaufman, S., et al, J. Biol. Chem., 234, 2683–2688, 10/59; Kaufman, S., J. Biol. Chem., 242, 3934–3943, Sep. 10, 1967), and the discovery in the course of the inventions herein that the continuous production of tetrahydrobiopterin, via a guanosine triphosphate pathway or a pterin salvage pathway, is not required for maintaining constitutive nitric oxide synthase activity over at least a period of hours.

It has been discovered herein that inhibiting the synthesis of tetrahydrobiopterin in vascular cells via the guanosine triphosphate pathway and/or the pterin salvage pathway selectively inhibits the induction of nitric oxide synthesis in said cells by bacterial endotoxins and cytokines, i.e., performs such inhibiting without affecting physiological constitutive enzyme-mediated nitric oxide synthesis. The inhibition of nitric oxide synthesis in smooth muscle cells in accordance with the invention is an unexpected result since it has been shown that macrophages which are "normal"i.e., are not induced for nitric oxide synthesis, already contain enough tetrahydrobiopterin for a maximal rate of nitric oxide synthesis (see Kwon, N. C., et al, J. Biol. Chem. 264:20496–2501, 1989).

In a first embodiment the invention herein is directed at a method of inhibiting induced nitric oxide synthesis from arginine in vascular cells in a subject in need of said inhibition (e.g,. for prophylaxis or treatment of systemic hypotension or to restore vascular contractile sensitivity to effects of pressor agents such as $\alpha_1$-adrenergic agents), said method comprising administering to said subject of a nitric oxide synthesis inhibiting therapeutically effective amount of (a) at least one guanosine triphosphate pathway tetrahydrobiopterin synthesis antagonist which is not a substrate for tetrahydrobiopterin synthesis via the pterin salvage pathway or (b) at least one pterin salvage pathway tetrahydrobiopterin synthesis antagonist or of both (a) and (b).

In a second embodiment, the invention herein is directed at a method of inhibiting induced nitric oxide synthesis from arginine in vascular cells in a subject in need of said inhibition (e.g., for prophylaxis or treatment of systemic hypotension or to restore vascular contractile sensitivity to effects of pressor agents such as $\alpha_1$-adrenergic agents), said method comprising administering to said subject of nitric oxide synthesis inhibiting therapeutically effective amounts of at least one guanosine triphosphate pathway tetrahydrobiopterin synthesis antagonist which is a reduced pterin that is a substrate for tetrahydrobiopterin synthesis via the pterin salvage pathway and of at least one pterin salvage pathway tetrahydrobiopterin synthesis antagonist.

An aspect of each embodiment is directed to prophylaxis or treatment of a subject for systemic hypotension caused by production of nitric oxide induced by therapy with cytokines, e.g., interferons including gamma-interferon, tumor necrosis factor, interleukin-1 or interleukin-2, e.g., chemotherapeutic treatment with tumor necrosis factor or interleukin-2, said method involving administering a therapeutically effective amount of said tetrahydrobiopterin synthesis antagonist(s) to a subject possibly developing or having such systemic hypotension.

A further aspect of each embodiment is directed to prophylaxis or treatment of a subject for systemic hypotension caused by production of nitric oxide induced by endotoxin from bacterial infection or other bacterial toxin, e.g., arising from immunosuppression therapy, said method involving administering a therapeutically effective amount of said tetrahydrobiopterin synthesis antagonist(s) to a subject possibly developing or having such systemic hypotension.

A further aspect of each embodiment is directed to prophylaxis or treatment of a subject for systemic hypotension caused by production of nitric oxide induced by therapy with cytokines, e.g., interferons including gamma-interferon, tumor necrosis factor, interleukin-1 or interleukin-2, e.g., chemotherapeutic treatment with tumor necrosis factor or interleukin-2, said method involving administering to the subject a pressor agent such as an $\alpha_1$-adrenergic agonist, e.g., phenylephrine, epinephrine, norepinephrine, dopamine, metaraminol, methoxamine, ephedrine, or mephentermine, in a therapeutically effective dosage and an amount of said tetrahydrobiopterin synthesis antagonist(s) to restore vascular sensitivity to effects of the pressor agent (i.e., to increase and/or prolong the efficacy of the $\alpha_1$-adrenergic agonists).

A still further aspect of each embodiment is directed to prophylaxis or treatment of a subject for systemic hypotension caused by production of nitric oxide induced by endotoxin from bacterial infection or other bacterial toxin, e.g., arising from immunosuppression therapy, said method involving administering to the subject possibly developing or having such systemic hypotension, a pressor agent such as an $\alpha_1$-adrenergic agonist, e.g., phenylephrine, epinephrine, norepinephrine, dopamine, metaraminol, methoxamine, ephedrine, or mephentermine, in a therapeutically effective amount (i.e., an amount to increase blood pressure) and an amount of said tetrahydrobiopterin synthesis antagonist(s) to restore vascular sensitivity to effects of the pressor agent (i.e., to increase and/or prolong the efficacy of the $\alpha_1$-adrenergic agonists).

Still a further aspect of each embodiment is directed to prophylaxis or treatment of a subject for systemic hypotension caused by production in vascular cells of nitric oxide induced by therapy with cytokines, e.g., gamma-interferon, tumor necrosis factor, interleukin-1 or interleukin-2, e.g., chemotherapeutic treatment with tumor necrosis factor or interleukin-2, said method involving inhibiting nitric oxide production in vascular cells by administering to a subject possibly developing or having such hypotension a therapeutically effective amount (i.e., a nitric oxide production limiting amount, i.e., a blood pressure raising amount) of said tetrahydrobiopterin synthesis antagonist(s) and a therapeutically effective amount (i.e., a nitric oxide production limiting amount, i.e., a blood pressure raising amount) of nitric oxide synthase inhibitor, e.g., arginine or citrulline analogs including $N^G$-methyl-L-arginine, $N^G$-amino-L-arginine, $N^G$-nitro-L-arginine, $N^G$-nitro-L-arginine methyl ester, $N^\delta$-iminomethyl-L-ornithine, or canavanine.

Yet a further aspect of each embodiment is directed to prophylaxis or treatment of a subject for systemic hypotension caused by production in vascular cells of nitric oxide induced by endotoxin from bacterial infection or other bacterial toxin, e.g., arising from immunosuppression therapy, said method involving inhibiting nitric oxide production in vascular cells by administering to a subject possibly developing or having such hypotension a therapeutically effective amount (i.e., a nitric oxide production limiting amount, i.e., a blood pressure raising amount) of said tetrahydrobiopterin synthesis antagonist(s) and a therapeutically effective amount (i.e., a nitric oxide production limiting amount, i.e., a blood pressure raising amount) of nitric oxide synthase inhibitor, e.g., arginine or citrulline analogs including $N^G$-methyl-L-arginine, $N^G$-amino-L-arginine, $N^G$-nitro-L-arginine, $N^G$-nitro-L-arginine methyl ester, $N^\delta$-iminomethyl-L-ornithine, or canavanine.

A different embodiment is directed to prophylaxis or treatment of a subject for inflammation, e.g., arising from non-acute allergic reactions including contact dermatitis, from autoimmune conditions including rheumatoid arthritis, and host-defense immune mechanisms, e.g., allograft rejection reactions, caused by immunologically induced nitric oxide production, said method involving inhibiting said nitric oxide production by administering to a subject possibly developing or having such inflammation, a nitric oxide synthesis inhibiting therapeutically effective (inflammation attenuating) amount of (a) at least one guanosine triphosphate pathway tetrahydrobiopterin synthesis antagonist which is not a substrate for tetrahydrobiopterin synthesis via the pterin salvage pathway or (a) and (b) at least one dihydrofolate reductase inhibitor.

Another different embodiment is directed to prophylaxis or treatment of a subject for inflammation, e.g., arising from non-acute allergic reactions including contact dermatitis, from autoimmune conditions including rheumatoid arthritis, and from host-defense immune mechanisms, e.g., allograft rejection reactions, caused by immunologically induced nitric oxide production, said method involving inhibiting said nitric oxide production by administering to a subject possibly developing or having such inflammation, nitric oxide synthesis inhibiting therapeutically effective (inflammation attenuating) amounts of at least one guanosine triphosphate pathway synthesis antagonist which is a reduced pterin that is a substrate for tetrahydrobiopterin synthesis via the pterin salvage pathway and at least one dihydrofolate reductase inhibitor.

An improvement on all of the above methods comprises also administering to said subject a catecholamine replacing non-toxic amount of levodopa with or without carbidopa and a serotonin replacing non-toxic amount of L-5-hydroxytryptophane to accommodate for depletion of levodopa and serotonin in the subject due to administration of the tetrahydrobiopterin synthesis antagonist(s) herein.

The term "subject" is used herein to mean any mammal, including humans, where nitric oxide formation from arginine occurs. The methods herein for use on subjects contemplate prophylactic use as well as curative use in therapy of an existing condition. When the combination of guanosine triphosphate pathway tetrahydrobiopterin synthesis antagonist and pterin salvage pathway tetrahydrobiopterin synthesis antagonist is used, the amounts used of each should be such that the combination inhibits induced nitric oxide synthesis from arginine.

The guanosine triphosphate pathway (also referred to as the tetrahydropterin pathway) for tetrahydrobiopterin synthesis is described in Nicol, C., et al, Ann. Rev. Biochem. 54, 729–764, 1985. It is considered to comprise the following: Guanosine triphosphate is converted to dihydroneopterin triphosphate in a reaction catalyzed by guanosine triphosphate cyclohydrolase I (GTP CHI; EC 3.5.4.16). In a second step, the dihydroneopterin is converted to an unstable intermediate in a reaction catalyzed by 6-pyruvoyl tetrahydropterin synthase. In a third and fourth step, the unstable intermediate is reduced to tetrahydrobiopterin in reactions mediated by sepiapterin reductase and a possible additional enzyme. GTP CHI is the rate-limiting enzyme for the induced guanosine triphosphate pathway.

The pterin salvage pathway (also referred to as the dihydropterin pathway) for tetrahydrobiopterin synthesis is described in Nicol, C., et al, Ann. Rev. Bioch. 54, 729–764, 1985. The final step of the pterin salvage pathway converts dihydrobiopterin into tetrahydrobiopterin in a reaction catalyzed by dihydrofolate reductase.

Below, LPS is used to mean bacterial lipopolysaccharide, IFN is used to mean interferon-gamma, DAHP is used to mean 2,4-diamino-6-hydroxypyrimidine, MTX is used to mean methotrexate and SEP is used to mean sepiapterin.

Figure 1A:
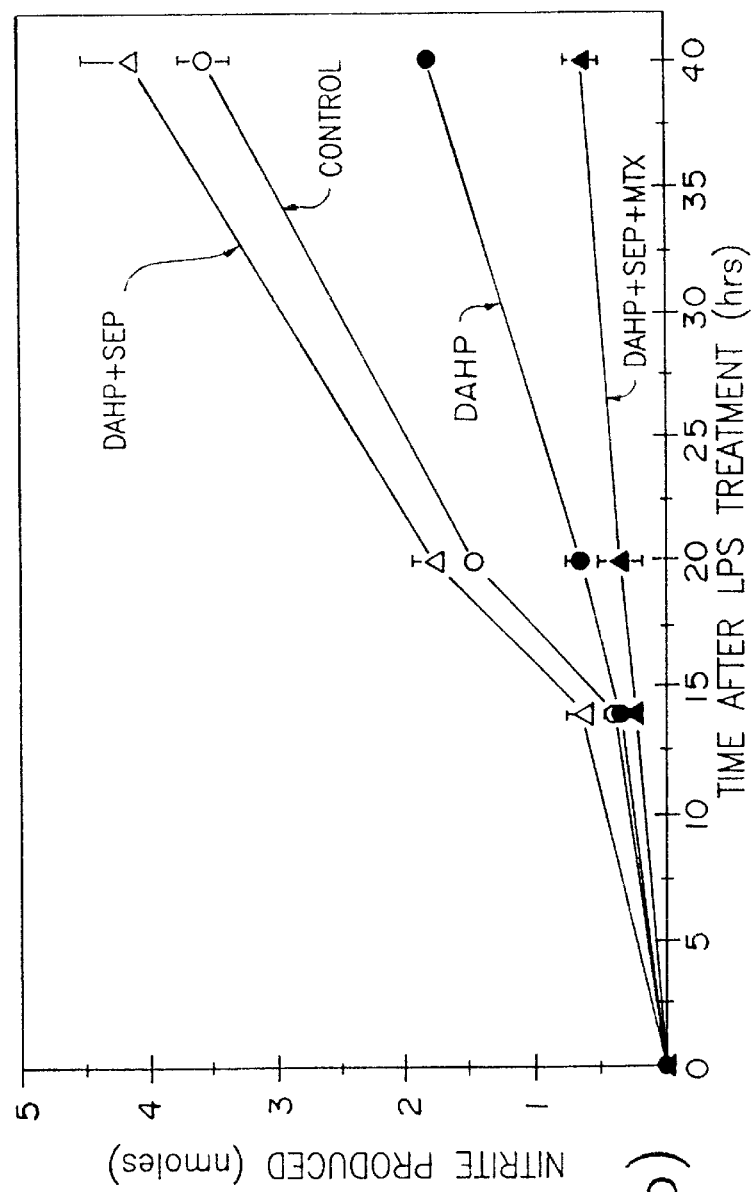
FIG. 1(a) is a graph depicting a concentration-response relationship for inhibition by DAHP (2,4-diamino-6-hydroxypyrimidine) of 24-hr. nitrite accumulation in a cell culture medium of rat aortic smooth muscle cells which are induced by bacterial lipopolysaccharide/interferon-gamma and depicts the results of Example I.

In all the figures, data symbols and bars are mean values and errorbars are standard errors of the mean.

DETAILED DESCRIPTION

Turning now to the first embodiment described above, the guanosine triphosphate pathway tetrahydrobiopterin synthesis antagonists which are not substrates for the pterin salvage pathway include agents selected from the group consisting of guanosine triphosphate cyclohydrolase I inhibitors, 6-pyruvoyl tetrahydrobiopterin synthase inhibitors and sepiapterin reductase inhibitors. The guanosine triphosphate cyclohydrolase I inhibitors include, for example, substituted pyrimidines, oxidized pterins and reduced pterins that are not substrates for the pterin salvage pathway. The substituted pyrimidines include hydroxyl, amino and halogen substituted pyrimidines, for example, 2,4-diamino-6-hydroxypyrimidine, 2,5-diamino-6-hydroxypyrimidine, 4,5-diamino-6-hydroxypyrimidine, 4,5-diaminopyrimidine, and 4,6-diamino-2-hydroxypyrimidine. The oxidized pterins include, for example, neopterin, xanthopterin, isoxanthopterin and biopterin. The reduced pterins that are not substrates for the pterin salvage pathway include, for example, 7,8-dihydro-D-neopterin, (6R,S)-5,6,7,8-tetrahydro-D-neopterin, 7,8-dihydrofolic acid and 5,6,7,8-tetrahydrofolic acid. Turning now to the 6-pyruvoyl tetrahydrobiopterin synthase inhibitors, none are currently known. Turning now to the sepiapterin reductase inhibitors, these include N-acetylserotonin, N-acetyldopamine, N-acetyl-m-tyramine, N-chloroacetyldopamine, N-chloroacetylserotonin, N-methoxyacetyldopamine and N-methoxyacetylserotonin.

Turning now to the second embodiment described above, the guanosine triphosphate pathway tetrahydrobiopterin synthesis antagonists which are reduced pterins that are substrates for tetrahydrobiopterin synthesis via the pterin salvage pathway; these include 7,8-dihydro-L-biopterin, and L-sepiapterin. The substrate 7,8-dihydro-L-biopterin may be provided by oxidation of (6R)-5,6,7,8-tetrahydro-L-biopterin.

Turning now to the pterin salvage pathway tetrahydrobiopterin synthesis antagonists, these are the same for the first and second embodiments and are dihydrofolate reductase inhibitors. These include, for example, methotrexate, aminopterin, 10-propargyl-5,8-dideazafolate; 2,4-diamino, 5-(3',4'-dichlorophenyl),6-methylpyrimidine; trimetrexate; pyrimethamine; trimethoprim; pyritrexim 5,10-dideazatetrahydrofolate; and 10-ethyl,10-deazaaminopterin.

The dosages of the tetrahydrobiopterin synthesis inhibitors for inhibiting vascular dysfunctions resulting from nitric oxide overproduction, e.g., hypotension and pressor hyporesponsivity, in vascular cells and for attenuating inflammation resulting from nitric oxide overproduction in immune cells, generally range from 1 $\mu$g/kg to 300 mg/kg with the actual dosage depending on the inhibitor selected. In the case of dihydrofolate reductase inhibitors which are already used clinically, conventional dosages for cancer chemotherapy apply in the case of acute conditions and conventional dosages now used for treatment of rheumatoid arthritis apply for treating inflammation. Where required, tetrahydrofolates (i.e., leucovorin) may be administered subsequently to salvage pathway inhibitors to alleviate toxicity in accordance with current usage for cancer chemotherapy or administered concurrently therewith to prevent toxicity arising from tetrahydrofolate synthesis inhibition. Preferably the inhibitors are administered intravenously for systemic hypotension because of the need for fast response. For other conditions where induced nitric oxide synthesis may be detrimental, e.g., in treating inflammation, immune-rejection phenomena and neurodegenerative diseases, other methods of administration may also be appropriate, e.g., oral, intrasynovial, subcutaneous, or intramuscular methods of administration. For inflammation, the above-recited dosages normally are daily dosages and are administered for a period of time required to deplete the very high level of tetrahydrobiopterin normally present in immune cells, i.e., two days or more, e.g., for two days to three weeks.

We turn now to the $\alpha_1$-adrenergic agonists. The $\alpha_1$-adrenergic agonists are used for the same purpose now (i.e., to increase blood pressure in a hypotensive patient) but eventually stop working because of loss of vascular contractile sensitivity. The $\alpha_1$-adrenergic agonists are currently used to treat hypotension in septic and cytokine treated patients. They are used herein in the same dosages as they are currently used, i.e., in conventional therapeutically effective amounts. As indicated above, suitable $\alpha_1$-adrenergic agonists include, for example, epinephrine, norepinephrine, dopamine, phenylephrine, metaraminol, methoxamine, ephedrine, and mephentermine. Doses for dopamine typically range from 2 $\mu$g/kg/min to 50 $\mu$g/kg/min. Doses for epinephrine typically range from 0.25 mg to 1.0 mg. Doses for norepinephrine typically range from 2 $\mu$g/min to 4 $\mu$g/min and are typically used if dopamine dose exceeds 20 $\mu$g/kg/min. Doses for phenylephrine can range from 0.1 to 10 $\mu$g/kg. The route of administration of the most popular $\alpha_1$-adrenergic agonists (epinephrine, norepinephrine and dopamine) is intravenous and for the others the route of administration is intravenous or in some cases subcutaneous.

We turn now to the nitric oxide synthase inhibitors. The dosages of these generally range from 0.1 to 100 mg/kg, with the actual dosage depending on the inhibitor selected. Doses for $N^G$-methyl-L-arginine range from 1 to 40 mg/kg. The route of administration is preferably intravenous or other route providing a fast response.

As indicated above, an embodiment herein is directed to blocking tetrabiopterin synthesis in vascular cells to inhibit nitric oxide synthesis from arginine in said cells in a subject in need of said inhibition, e.g., a subject suffering from vascular dysfunction because of pathological overproduction of nitric oxide induced in said cells by cytokines and/or bacterial endotoxins. This is accomplished by administering to the subject of a nitric oxide synthesis inhibiting therapeutically effective amount of (a) at least one guanosine triphosphate pathway tetrahydrobiopterin synthesis antagonist which is not a substrate for tetrahydrobiopterin synthesis via the pterin salvage pathway, e.g., 2,4-diamino-6-hydroxypyrimidine (DAHP) or (b) at least one pterin salvage pathway tetrahydrobiopterin synthesis antagonist, e.g., a dihydrofolate reductase inhibitor such as methotrexate, or both (a) and (b), or by administering to the subject of nitric oxide synthesis inhibiting therapeutically effective amounts of at least one guanosine triphosphate pathway tetrahydrobiopterin synthesis which is a reduced pterin that is a substrate for tetrahydrobiopterin synthesis via the pterin salvage pathway, e.g., L-sepiapterin and of at least one pterin salvage pathway tetrahydrobiopterin synthesis antagonist, e.g., a dihydrofolate reductase inhibitor such as methotrexate.

As indicated above, another embodiment herein is directed to blocking tetrahydrobiopterin synthesis in immune cells to inhibit nitric oxide production therein for prophylaxis or treatment of inflammation due to nitric oxide overproduction in immune cells.

Tetrahydrobiopterin is not only involved in the synthesis of nitric oxide from arginine in vascular cells and in the synthesis of nitric oxide from arginine in immune cells, but it is also involved in the synthesis of catecholamines (epinephrine, norepinephrine and dopamine) and in the synthesis of serotonin in other cells (catecholamines are synthesized in neuronal, adrenal, liver and kidney cells and serotonin is synthesized in neuronal, mast and liver cells), and administration of tetrahydrobiopterin synthesis antagonists in the embodiments herein, besides blocking tetrahydrobiopterin synthesis in vascular cells and in immune cells, can also block synthesis of tetrahydrobiopterin in said other cells thereby causing a deficiency in synthesis of catecholamines (norepinephrine, epinephrine and dopamine) and/or serotonin, with the additional result of unwanted counterproductive effects and/or side effects.

Norepinephrine is a sympathetic transmitter released by nerves and maintains tonic constrictory tone on blood vessels in healthy individuals. Epinephrine is a hormone from the adrenal gland which is produced on demand to increase tonic constrictory tone. These ordinarily maintain blood pressure in a normal range. Thus, inhibition of tetrahydrobiopterin synthesis which interferes with the production of these decreases blood pressure and is counterproductive to interfering with nitric oxide production to increase blood pressure. Catecholamines including norepinephrine, epinephrine and dopamine are neurotransmitters in the brain; depletion of these can cause neurological symptoms, e.g., convulsions, disturbances of tone and posture, drowsiness, irritability, abnormal movements, recurrent hyperthermia (without infection), hypersalivation and swallowing difficulties. An improvement on the inventions herein involves administering to the subjects being treated by the aforedescribed methods herein a catecholamine replacing non-toxic amount of levodopa, typically ranging from about 1 to about 175 mg/kg/day, preferably ranging from 5 to 20 mg/kg/day. Administration is for the number of days for which neurological symptoms persist and for which catecholamine depleting administrations are carried out. Preferably, administration is carried out intravenously. For humans, each day's dose is preferably administered as a continuous infusion over 2 to 24 hours. The levodopa is preferably administered in combination with carbidopa, e.g., in a weight ratio of levodopa:carbidopa ranging from 2:1 to 15:1; this allows reduction in the dosage of the levodopa to a preferred range of 2 to 10 mg/kg/day.

Serotonin is a neurotransmitter. Inhibition of tetrahydrobiopterin synthesis which interferes with the production of this can interfere with interaction with serotonin receptors and can result in neurological symptoms and where serotonin production is substantially inhibited, even death. An improvement on the aforedescribed methods herein involves administering to the subject being treated by the aforedescribed methods herein a serotonin replacing non-toxic amount of L-5-hydroxytryptophane, typically ranging from about 1 to about 50 mg/kg/day, preferably ranging from 5 to 20 mg/kg/day. Administration is for the number of days for which neurological symptoms persist and for which serotonin depleting administrations are carried out. Preferably, administration is carried out intravenously. For humans, each day's dose is preferably administered as a continuous infusion over 2 to 24 hours.

The term "catecholamine replacing amount" is used herein to mean an amount sufficient to eliminate or ameliorate any symptoms that would be caused by catecholamine deficiency due to blocking of tetrahydrobiopterin synthesis if the levodopa were not administered.

The term "serotonin replacing amount" is used herein to mean an amount sufficient to eliminate or ameliorate any symptoms that would be caused by serotonin deficiency due to blocking of tetrahydrobiopterin synthesis if the L-5-hydroxytryptophane were not administered.

The improvements on the inventions herein to reduce or eliminate unwanted side effects provide methods as follows:

A first embodiment is directed to the method of inhibiting nitric oxide synthesis from arginine in vascular cells in a subject suffering from vascular dysfunction because of pathological overproduction of nitric oxide induced in said cells by cytokines and/or bacterial endotoxins, said method comprising administering to said subject of a nitric oxide synthesis inhibiting therapeutically effective amount of (a) at least one guanosine triphosphate pathway tetrahydrobiopterin synthesis antagonist which is not a substrate for tetrahydrobiopterin synthesis via the pterin salvage pathway or (b) at least one dihydrofolate reductase inhibitor or both (a) and (b) and also administering to said subject of a catecholamine replacing non-toxic amount of levodopa with or without carbidopa and a serotonin replacing non-toxic amount of L-5-hydroxytryptophane.

A second embodiment is directed to the method of inhibiting nitric oxide synthesis from arginine in vascular cells in a subject suffering from vascular dysfunction because of pathological overproduction of nitric oxide induced in said cells by cytokines and/or bacterial endotoxins, said method comprising administering to said subject of nitric oxide synthesis therapeutically effective amounts of at least one guanosine triphosphate pathway tetrahydrobiopterin synthesis antagonist which is a reduced pterin that is a substrate for tetrahydrobiopterin synthesis via the pterin salvage pathway and at least one dihydrofolate reductase inhibitor and also administering to said subject of a catecholamine replacing non-toxic amount of levodopa with or without carbidopa and a serotonin replacing non-toxic amount of L-5-hydroxytryptophane.

These two embodiments contemplate administration of tetrahydrobiopterin synthesis antagonist(s) as the only nitric oxide production inhibitor or together with nitric oxide synthase inhibitor or together with $\alpha_1$-adrenergic agonist.

A third embodiment herein is directed to a method of prophylaxis or treatment of a subject for inflammation caused by induced nitric oxide production from arginine in immune cells, said method involving inhibiting nitric oxide production in said cells by administering to a subject possibly developing or having such inflammation, a nitric oxide production limiting (inflammation attenuating) amount of (a) at least one guanosine triphosphate pathway synthesis antagonist which is not a substrate for tetrahydrobiopterin synthesis via the pterin salvage pathway or (b) at least one dihydrofolate reductase inhibitor or (a) and (b) and also administering to said subject of (c) a catecholamine replacing non-toxic amount of levodopa with or without carbidopa and (d) a serotonin replacing non-toxic amount of L-5-hydroxytryptophane.

A fourth embodiment is directed to a method of prophylaxis or treatment of a subject for inflammation caused by induced nitric oxide production from arginine in immune cells, said method involving inhibiting nitric oxide production in said cells by administering to a subject possibly developing or having such inflammation, nitric oxide production inhibiting (inflammation attenuating) amounts of at least one guanosine triphosphate pathway synthesis antagonist which is a reduced pterin that is a substrate for tetrahydrobiopterin synthesis via the pterin salvage pathway and at least one dihydrofolate reductase inhibitor and also administering to said subject of a catecholamine replacing non-toxic amount of levodopa with or without carbidopa and a serotonin replacing non-toxic amount of L-5-hydroxytryptophane.

The following examples are illustrative of the concepts of the invention and represent the best mode known to the inventor at this time.

EXAMPLE I

Aortic smooth muscle cells were cultured by explanting segments of the medial layer of aortae from adult male Fischer 344 rats. Aortae were removed aseptically and freed of adventitial and endothelial cells by scraping both the lumenal and abluminal surfaces. Medial fragments (1–2 mm) were allowed to attach to dry Primaria 25 cm$^2$ tissue culture flasks (Falcon; Oxnard, Calif.) which were kept moist with growth medium until cells emerged. Cultures were fed twice weekly with medium 199 containing 10% fetal bovine serum, 25 mM HEPES, 2 mM L-glutamine, 40 µg/ml endothelial cell growth supplement (Biomedical Technologies; Stoughton, Mass.) and 10 pg/ml gentamycin (GIBCO; Grand Island, N.Y.). When primary cultures became confluent, they were passaged by trypsinization and the explants were discarded. Cells in passage 10–15 were seeded at 20,000/well in 96-well plates.

When the cells became confluent (density of 60–80×10$^3$ cells in a well), the medium was removed by suction and fresh medium consisting of 200 µl of RPMI 1640 (Whittaker Laboratories) containing 10% bovine calf serum, 2.5 mM glutamine and penicillin (80 U/ml), streptomycin (80 µg/ml) and fugizone (2 µg/ml) was added to each well via a pipette.

Groups of 4 wells were each administered fixed concentrations of 2,4-diamino-6-hydroxypyrimidine (DAHP), namely 30 μg/ml, 100 μg/ml, 300 μg/ml, 1000 μg/ml and 3000 μg/ml, and a control was provided of wells which received no DAHP. To each was also added bacterial lipopolysaccharide (endotoxin; Serotype: *E. Coli.* 0111:B4, 50 μg/ml) plus rat interferon-gamma (50 mg/ml). The wells were then incubated at 37° C. in a humidified incubator for 24 hours. After this time, nitrite accumulation in the cell culture media was measured. Nitrite was measured by adding 100 μl of cell culture medium to 100 μl of Greiss reagent (0.5% sulfanilamide and 0.05% naphthylethylene-diamine dihydrochloride in 2.5% phosphoric acid) and $OD_{550}nm$ (an optical density of 550 nm) was immediately measured using a microplate reader (Molecular Devices; Menlo Park, Calif.). Nitrite concentrations were determined by comparison with standard solutions of sodium nitrite prepared in culture medium. Background nitrite levels in smooth muscle cell cultures not exposed to cytokines were subtracted from experimental values.

Figure 1B:
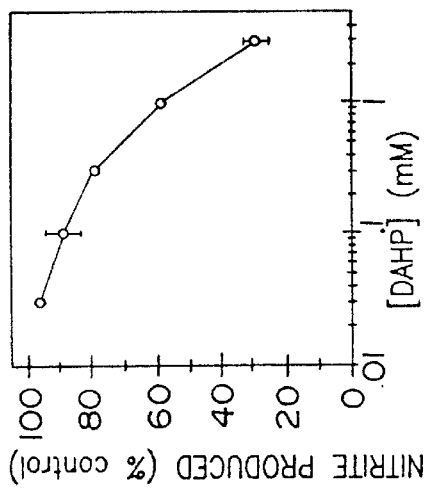
FIG. 1(b) depicts the time course of nitrite synthesis in response to LPS (bacterial lipopolysaccharide) and interferon-gamma on addition of additives including DAHP (2,4-diamino-6-hydroxypyridine), SEP (sepiapterin) and MTX (methotrexate) and shows the results of Example II.

Nitrite production is shown in FIG. 1(*a*). The results show that increasing concentrations of DAHP progressively inhibit nitrite production. Separate experiments (not explained here) showed that the nitrite production is a direct indicator of nitric oxide synthesis. Thus, this experiment shows that DAHP inhibits nitric oxide production.

EXAMPLE II

Example I was repeated except samples of cell culture media were collected at 14 hours, 20 hours and 40 hours. The cells were incubated with 2 mM DAHP or no DAHP (4 replicates for each time). The results are shown in FIG. 1(*b*) in the curves denoted CONTROL and DAHP. The results showed that the DAHP reduced the release of nitric oxide over time.

In another case the DAHP was added together with 100 μm sepiapterin (SEP). The results are shown in the curve in FIG. 1(*b*) in the curve denoted DAHP+SEP. The results show that sepiapterin overcame the blockade of nitric oxide synthesis caused by DAHP. This indicates that the mechanism of DAHP inhibition is specifically by blocking tetrahydrobiopterin synthesis from guanosine triphosphate since it is known that sepiapterin can form tetrahydrobiopterin by the alternate pterin salvage pathway.

In another case methotrexate (10 μM) was added together with the DAHP and sepiapterin. The results are shown in FIG. 1(*b*) in the curve denoted DAHP+SEP+MTX. The results show that sepiapterin was unable to overcome the inhibition of nitric oxide synthesis caused by DAHP. Since methotrexate is well known to be a potent and selective inhibitor of dihydrofolate reductase, and therefore blocks the pterin salvage pathway, this result indicates that blocking both pathways for tetrahydrobiopterin synthesis completely eliminates the induction of nitric oxide synthesis in smooth muscle cells by the combination of endotoxin and cytokine.

EXAMPLE III

Figure 2B:
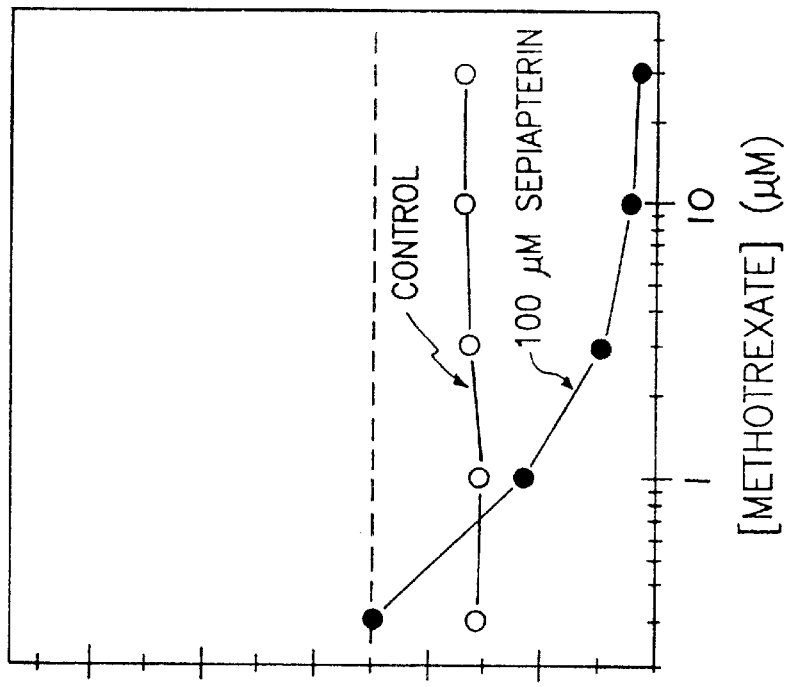
FIG. 2(b) depicts how the nitrite production response to bacterial lipopolysaccharide and interferon-gamma is affected by methotrexate both alone (CONTROL) and in the presence of sepiapterin and shows results of Example IV.
Figure 2A:
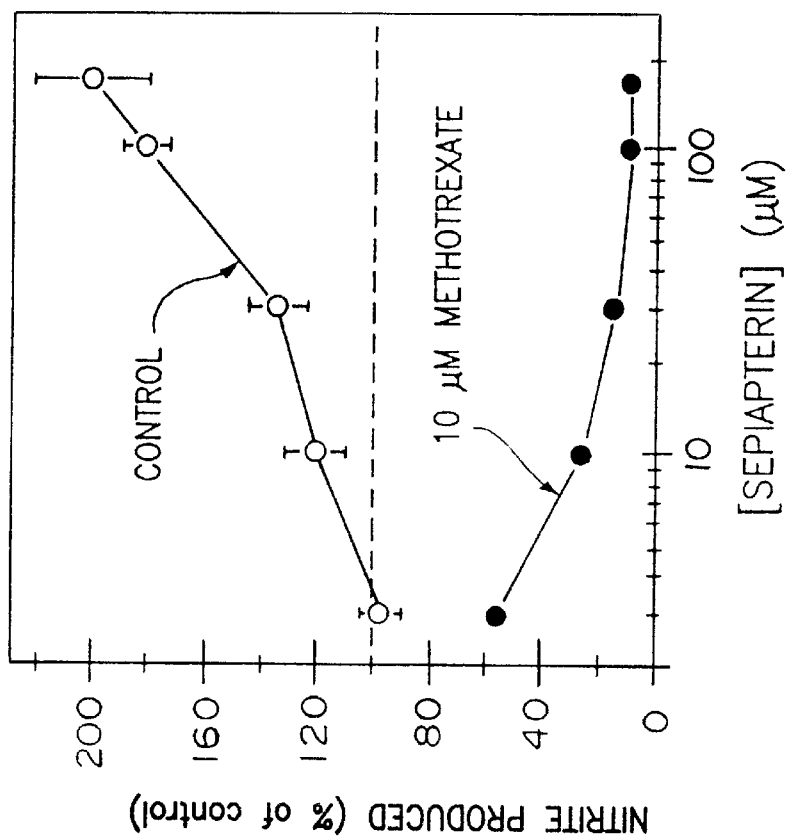
FIG. 2(a) depicts how the nitrite production response of rat aortic smooth muscle cells to bacterial lipopolysaccharide and interferon gamma is affected by sepiapterin both alone (CONTROL) and in the presence of methotrexate and shows results of Example III.

An experiment was carried out the same as in Example I except that sepiapterin was added instead of DAHP, in concentrations of 3, 10, 30, 100 and 300 μM, in the presence or absence (control) of 10 μM methotrexate. The results are shown in FIG. 2(*a*). The results show that sepiapterin causes an increase of induced nitric oxide production. Since sepiapterin directly forms tetrahydrobiopterin in the pterin salvage pathway, this indicates that tetrahydrobiopterin is rate limiting for nitric oxide synthesis in vascular cells. In contrast, when methotrexate was present, sepiapterin completely inhibited induced nitric oxide synthesis. This indicates that when the pterin salvage pathway is blocked (by the methotrexate), the sepiapterin functions as a GTP CHI inhibitor to block the guanosine triphosphate pathway and that when both pathways for tetrahydrobiopterin synthesis are blocked, induced nitric oxide synthesis does not occur.

EXAMPLE IV

An experiment was carried out the same as in Example I except that methotrexate was added instead of DAHP in concentrations of 0.3, 1, 3, 10 and 30 μM, in the presence or absence (control) of 100 μM sepiapterin. The results are shown in FIG. 2(*b*). The results show that maximally effective concentrations of methotrexate inhibit 30–40% of induced nitric oxide synthesis, and that, when sepiapterin is present, methotrexate completely inhibits induced nitric oxide synthesis, indicating that sepiapterin blocks the guanosine triphosphate pathway and that when both pathways for tetrahydrobiopterin synthesis are blocked, induced nitric oxide synthesis in vascular cells does not occur.

EXAMPLE V

Figure 3:
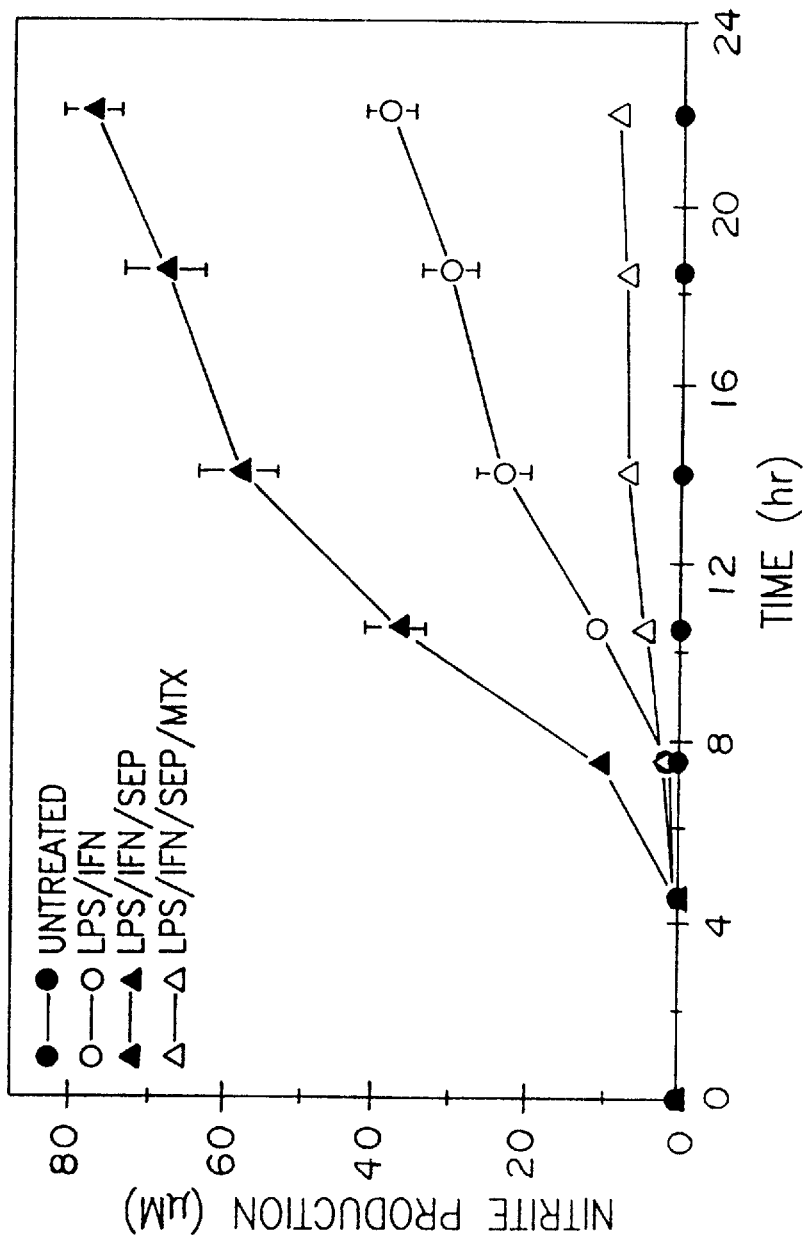
FIG. 3 depicts a time course of LPS (bacterial lipopolysaccharide) and IFN (interferon-gamma) induced nitrite synthesis of rat aortic smooth muscle cells and how it is affected by SEP (sepiapterin) both alone and in the presence of MTX (methotrexate) and shows results of Example V.

An experiment was carried out to study the time course of induced nitric oxide synthesis. Nitric oxide synthesis was induced by bacterial lipopolysaccharide and rat interferon-gamma as in Example I. Nitric oxide synthesis commenced after a delay of about 8 hours. When the same experiment was performed in the presence of 100 μM sepiapterin, nitric oxide production commenced earlier and was increased in amount at all times studied indicating that the availability of tetrahydrobiopterin is rate limiting for the onset and degree of induced nitric oxide production. Methotrexate (used in 10 μM concentration) in combination with sepiapterin caused a near complete inhibition of induced nitric oxide synthesis consistent with results of previous examples. The results of this experiment are depicted in FIG. 3.

EXAMPLE VI

An experiment is carried out the same as in Example I except that tetrahydrobiopterin is added instead of DAHP, in concentrations of 3, 10, 30, 100 and 300 μM in the presence or absence (control) of 10 μM methotrexate. The results are that tetrahydrobiopterin alone causes a small increase in induced nitric oxide synthesis. However, when methotrexate is present, tetrahydrobiopterin inhibits induced nitric oxide synthesis, indicating that tetrahydrobiopterin does not enter cells directly and is first oxidized and further that the tetrahydrobiopterin inhibits the guanosine triphosphate pathway of vascular cells.

EXAMPLE VII

Figure 4:
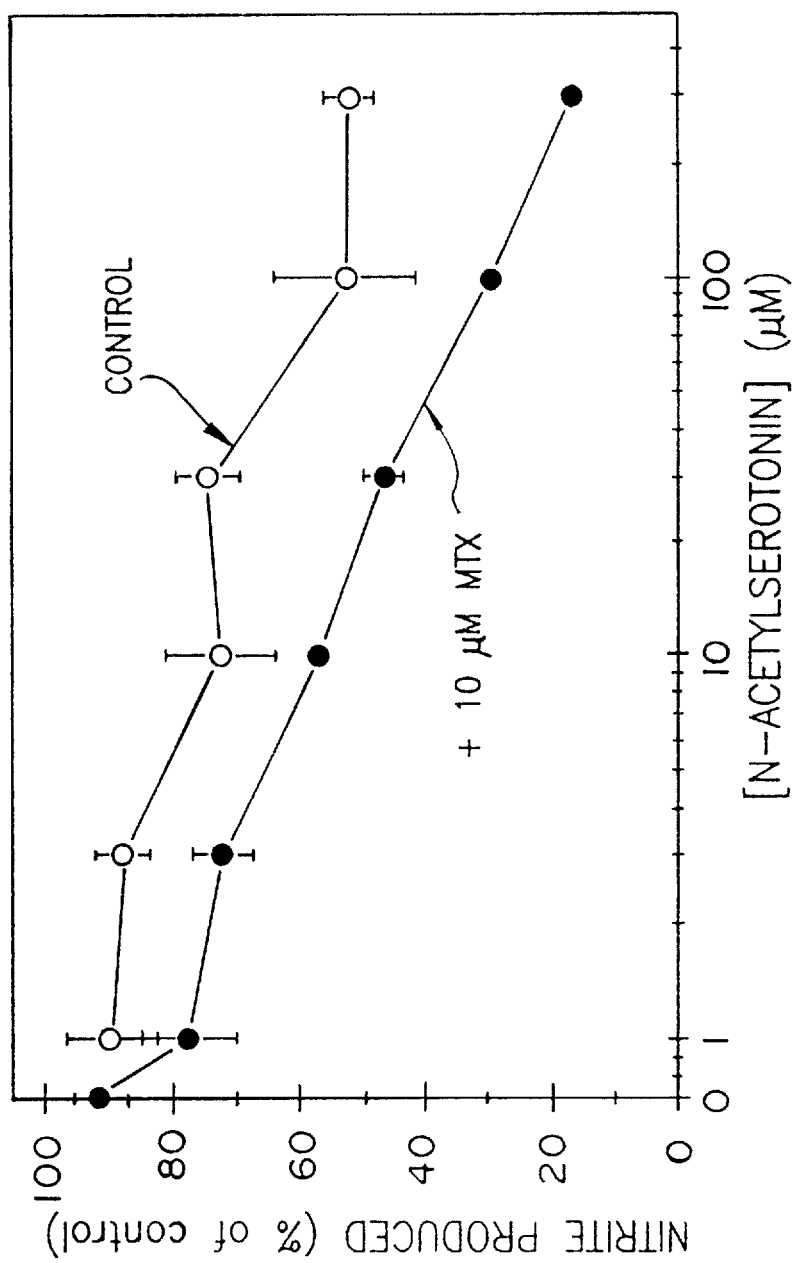
FIG. 4 depicts how the nitrite production response of rat aortic smooth muscle cells to bacterial lipopolipaccharide and interferon-gamma is affected by N-acetylserotonin both alone (CONTROL) and in the presence of MTX (methotrexate) and shows results of Example VII.

An experiment was carried out the same as in Example I except that N-acetylserotonin was used instead of DAHP, at concentrations of 1, 3, 10, 30, 100 and 300 μM, in the presence or absence (control) of 10 μM methotrexate. The results are shown in FIG. 4. The results show that when N-acetylserotonin is given alone, the induced nitric oxide synthesis is inhibited maximally by approximately 50%. However, when methotrexate was present, a near complete inhibition is shown. This demonstrates that N-acetylseratonin blocks the guanosine triphosphate pathway and that inhibition of both pathways of tetrahydrobiopterin synthesis is necessary for maximal nitric oxide synthesis inhibition.

EXAMPLE VIII

Rat aortic smooth muscle cells are prepared as in Example I except that they are grown to confluence in 75 $cm^2$ tissue culture flasks.

Figure 5:
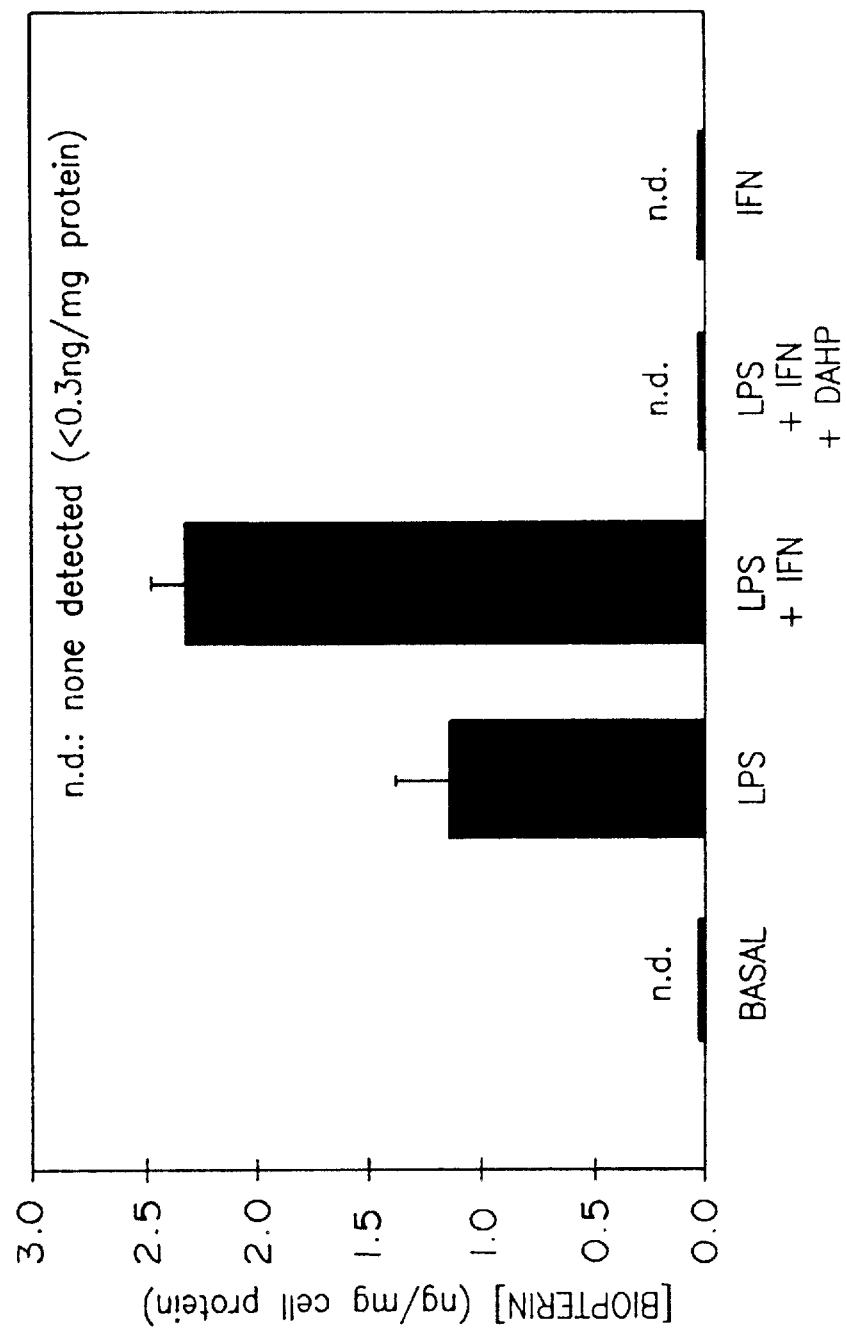
FIG. 5 depicts the biopterin content of smooth muscle cells under basal conditions and after treatment for 12 hours with various additives including LPS (bacterial lipopolysaccharide), IFN (interferon-gamma), and DAHP (2,4-diamino-6-hydroxypyrimidine) and shows results of Example VIII.

Groups of flasks (6 to a group) were treated with no additive (BASAL), bacterial lipopolysaccharide (LPS) as in Example I, LPS as in Example I and interferon-gamma (IFN) as in Example I, LPS and IFN as in Example I and DAHP (3 mM) and IFN (as in Example I) alone. After 12 hours incubation in a humidified incubator at 37° C., cells were harvested with a Teflon cell scraper, lysed by three cycles of freezing and thawing in liquid nitrogen and a 37° C. water bath. The cell lysate was centrifuged at 12000 RPM in a Beckman Microfuge. The supernatants were recovered and acidified with 1N HCl, and the pterins present were oxidized by addition of $KI/I_2$ solution (1% $I_2$, 2% KI in 1N HCL), and incubated at 37° C. for 1 hour in the dark. Excess I2 was removed by treatment with 0.1M ascorbic acid. Samples were made pH 7.8 with 1N NaOH and 200 mM TRIS buffer and subjected to HPLC analysis for total biopterin content using a reverse phase $C_{18}$ column (Beckman, 3 micron) and fluorescence detection with excitation at 356 nm and emission at 445 nm. The results are shown in FIG. 5. As shown in FIG. 5, untreated smooth muscle cells and interferon-treated smooth muscle cells do not have detectable levels of biopterin. However as indicated in FIG. 5, endotoxin (LPS) treated smooth muscle cells contain significant amounts of biopterin and this biopterin content was further increased by interferon (IFN). Most importantly as indicated in FIG. 5., DAHP completely abolished the increase in cellular biopterin caused by LPS and IFN.

EXAMPLE IX

Figure 6:
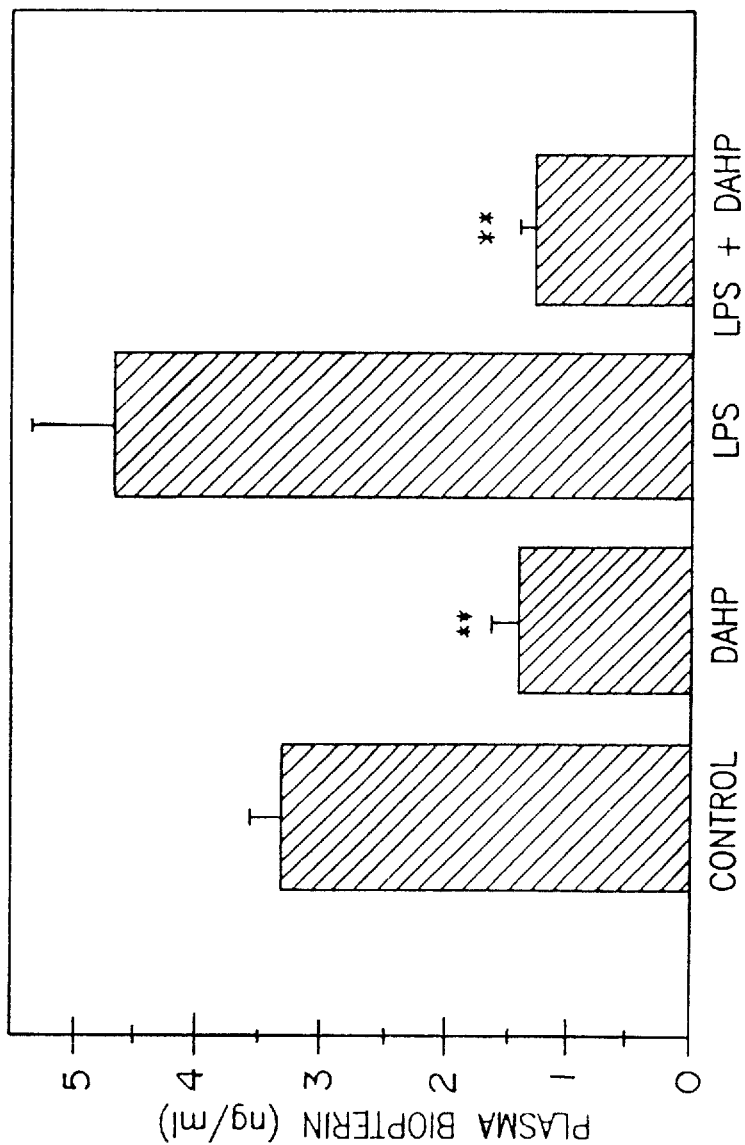
FIG. 6 depicts plasma biopterin levels in rats and how they are affected by agents including DAHP (2,4-diamino-6-hydroxypyrimidine) and LPS (bacterial lipopolysaccharide) and shows results of Example IX. The asterisks above an error bar indicate a statistically significant reduction in biopterin (relative to control) with $p<0.01$ determined by student's t-test.

Groups of 6 to 20 Sprague-Dawley rats (250–300 g) were injected with no agent (control), DAHP (1 g/kg intraperitonially), LPS 15 mg/kg, i.p.) and the combination of the DAHP and LPS. After 6 hours, animals were anesthetized with ether and blood was drawn by cardiac puncture. Plasma was obtained by centrifugation and total biopterin levels were measured as in Example VIII. The results are shown in FIG. 6. As shown in FIG. 6, DAHP reduced the control concentration of plasma biopterin by greater than 50% and completely abolished the elevated plasma biopterin concentration caused by LPS. This shows that DAHP is effective in vivo in blocking tetrahydrobiopterin synthesis.

EXAMPLE X

Figure 7:
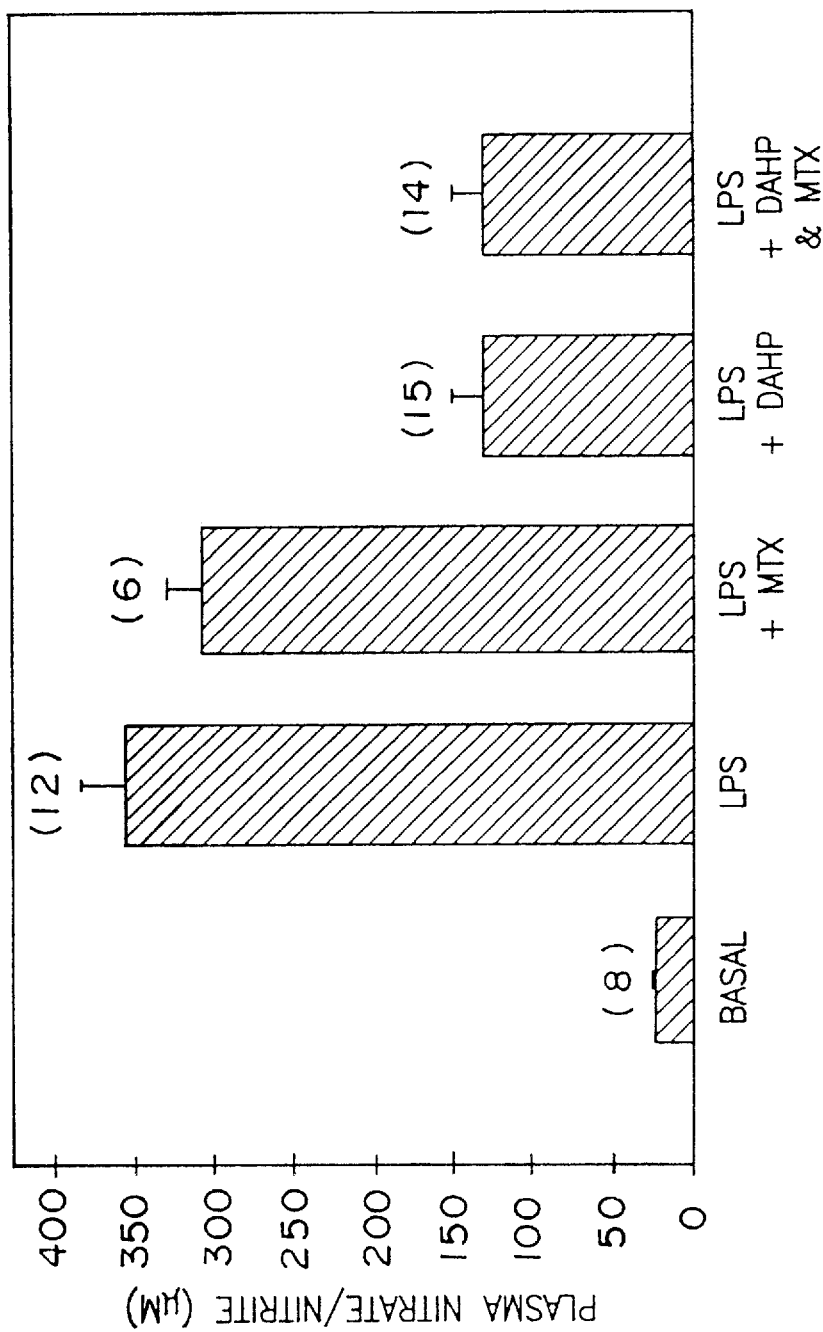
FIG. 7 depicts plasma nitrate/nitrite levels in rats and how they are affected by agents including LPS (bacterial lipopolysaccharide), MTX (methotrexate) and DAHP (2,4-diamino-6-hydroxypyrimidine) and shows results of Example X. The numbers in parenthesis indicate the number of rats for the determination.

Groups of 6 to 15 Sprague-Dawley rats (250–300 g) were injected i.p. with no agents (BASAL), LPS (15 mg/kg), LPS at 15 mg/kg plus methotrexate (MTX) at 10 mg/kg, LPS (15 mg/kg) plus DAHP (1 g/kg) and LPS (15 mg/kg) plus DAHP (1 g/kg) plus MTX (10 mg/kg). After 6 hours animals were anesthetized with ether and blood was drawn by cardiac puncture. Plasma was obtained by centrifugation and the total of nitrate and nitrite concentration was measured by an automated calorimetric assay. In the assay, an automatic sample injector was used to apply samples to a copper-coated cadmium column for catalytic reduction of nitrate to nitrite. Samples were then mixed on-line with a stream of buffer-containing (10 g/l sulfanilamide, 1 g/l naphthalinediamine and 5% ortho-phosphoric acid). Nitrate/nitrite concentration was measured based on optical density (O.D.) at 546 nm using authentic nitrite as a reference standard. The results are shown in FIG. 7. As indicated in FIG. 7, LPS caused a 28-fold increase in serum nitrate/nitrite, this was slightly reduced by methotrexate but markedly reduced by DAHP in the absence or presence of methotrexate. This demonstrates that DAHP is an effective inhibitor of LPS-induced nitric oxide production in vivo.

EXAMPLE XI

Figure 8:
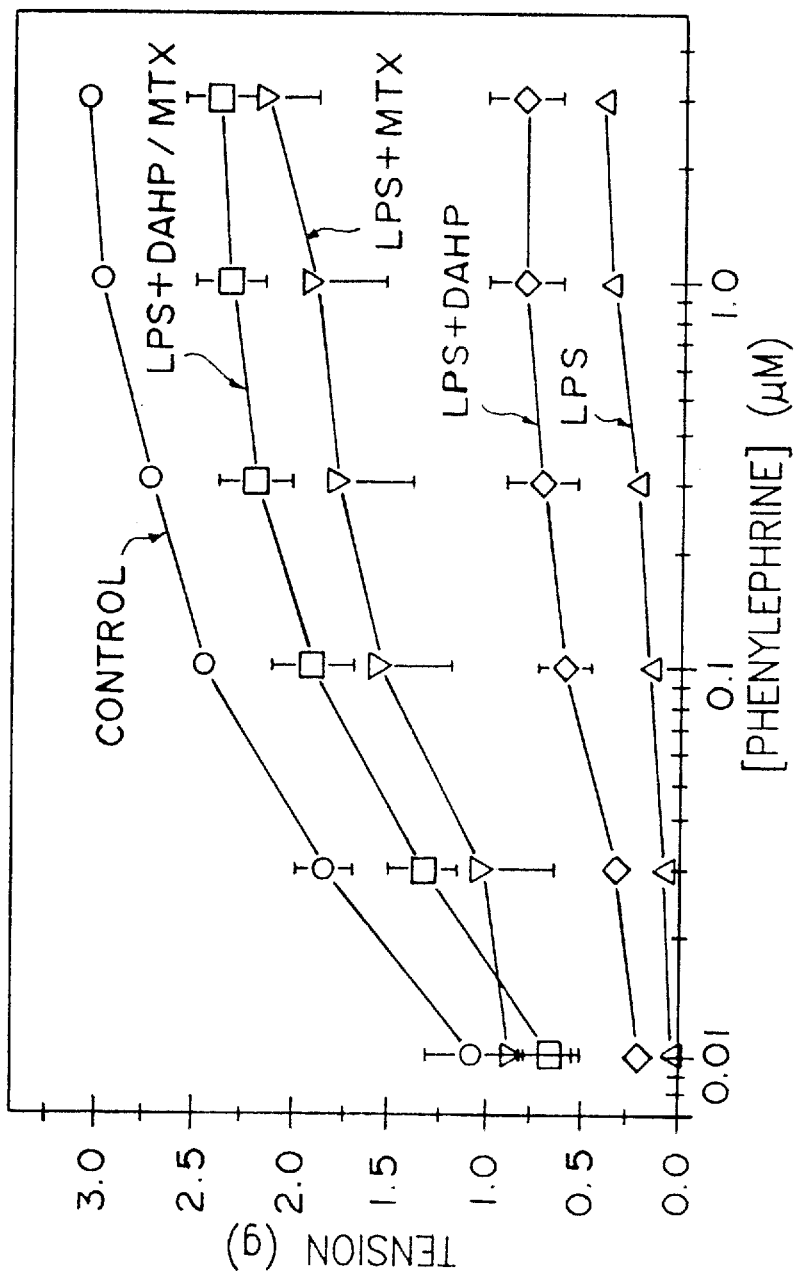
FIG. 8 depicts phenylephrine induced constrictory responses of isolated aortic rings prepared from rats that have been pretreated with agents including LPS (bacterial lipopolysaccharide), MTX (methotrexate) and DAPH (2,4-diamino-6-hydroxypyrimidine) and shows results of Example XI.

Groups of rats (6–10 per group) were either untreated, i.p. injected with LPS (15 mg/kg), i.p. injected with the LPS plus DAHP (1 g/kg), i.p. injected with the LPS plus MTX (10 mg/kg), and i.p. injected with the combination of the LPS, the DAHP and the MTX. After 6 hours, the rats were sacrificed and their thoracic aortae were removed and immersed in oxygenated Kreb's solution at 37° C. The Krebs' solution had the following composition in mM: NaCl, 110; KCl, 4.8; $CaC_2$, 2.5, $KH_2PO_4$, 1.2; $NaHCO_3$, 25; and dextrose, 11. Two to three mm wide rings were cut from the aortae and mounted in an organ bath for measurement of contractile tension. Rings were equilibrated in oxygenated Kreb's solution under 2 gm of tension. After a 1 hour equilibration, contractile response to phenylephrine were determined by cumulative dose response analysis. The results are shown in FIG. 8. As indicated in FIG. 8, LPS almost completely eliminated the constrictor response caused by the $\alpha_1$-adrenergic agonist phenylephrine, DAHP slightly overcame this inhibition by LPS of phenylephrine response, whereas MTX markedly restored phenylephrine sensitivity and the combination of DAHP and MTX was more effective than either agent alone. This shows that tetrahydrobiopterin synthesis inhibitors can block in vivo nitric oxide production and thereby restore vascular contractile sensitivity to pressor drugs.

EXAMPLE XII

Figure 9:
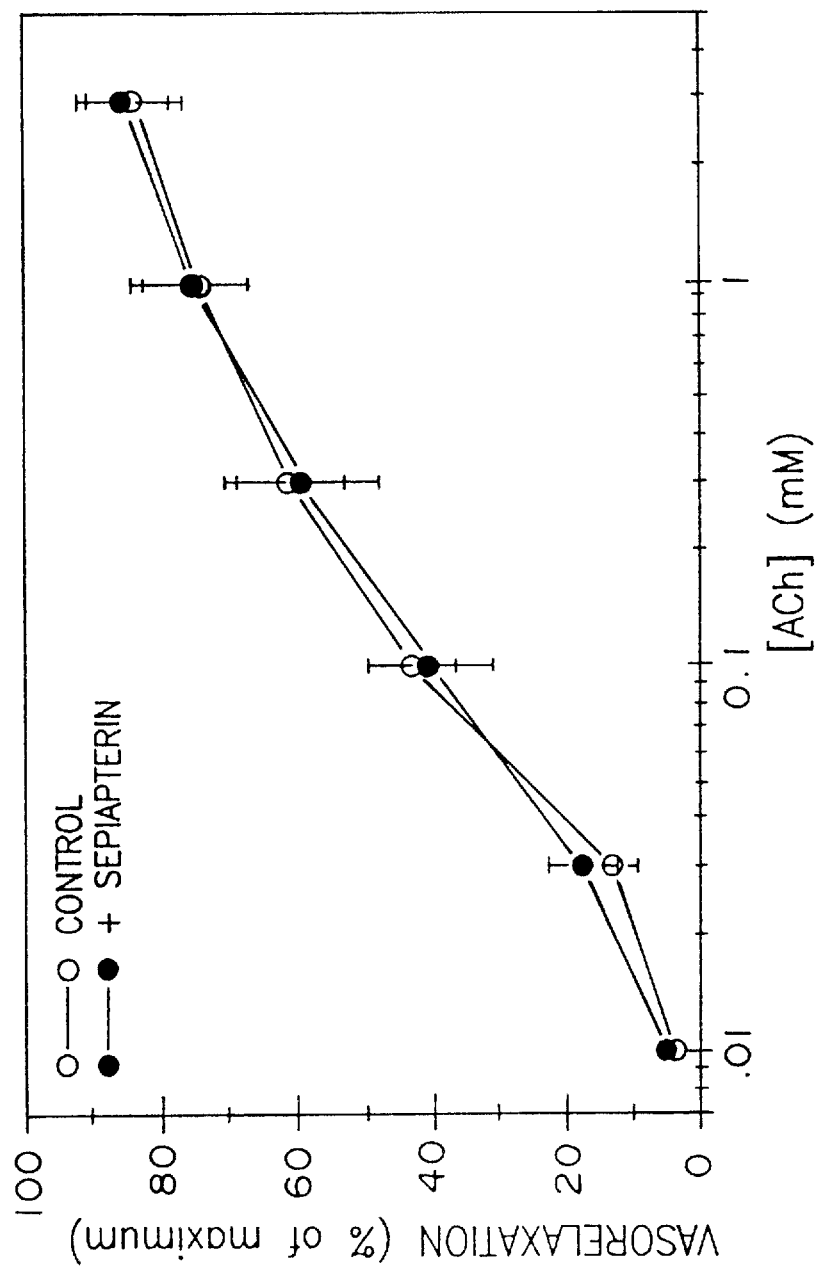
FIG. 9 depicts vasodilatory responses of isolated rat aortic rings to ACh (acetylcholine) before (CONTROL) and after treatment with sepiapterin.

As in Example XI rats were sacrificed and thoracic aortae isolated and rings were prepared in organ baths for tension recording. The rings were preconstricted with phenylephrine (0.3 $\mu$M) and relaxation was measured upon progressive and cumulative addition of acetylcholine (ACh) to the organ baths. Experiments were performed using 4 to 8 replicate rings before, and 30 minutes after exposure to sepiapterin (100 $\mu$M). The results are shown in FIG. 9. As indicated in FIG. 9, the sepiapterin did not at all alter the ability of acetylcholine to cause vasorelaxation. This indicates that constitutive nitric oxide synthase which is present in endothelial cells is not limited by tetrahydrobiopterin availability. When methotrexate (10 $\mu$M) is substituted for the sepiapterin, the same results are obtained. Thus, de novo synthesis (guanosine triphosphate pathway synthesis) of tetrahydrobiopterin is not required to maintain constitutive nitric oxide synthesis in endothelial cells over at least several hours.

When in the above examples, N-acetylserotonin replaces DAHP, in vivo similar results to what are obtained with DAPH, can be obtained.

When in the above examples, other pyrimidines, e.g. 2,5-diamino-6-hydroxypyrimidine, 2,4-diamino-6-hydroxypyrimidine or 4,6-diamino-2-hydroxypyrimidine, replace DAHP, similar guanosine triphosphate passageway blocking results are obtained.

When the above examples, other pterins replace sepiapterin, especially reduced pterins, e.g., (6R)-5,6,7,8-tetrahydro-L-biopterin, 7,8-dihydro-L-biopterin or 7,8-dihydro-D-neopterin, or 5,6,7,8-tetrahydro-D-neopterin or dihydrofolic acid or tetrahydrofolic acid or D,L-6-methyl-5,6,7,8-tetrahydropterin or 2-amino-6,7-dimethyl-4-hydroxy-5,6,7,8-tetrahydropteridine, similar guanosine triphosphate pathway blocking results are obtained and in same cases the reduced pterins also act as substrates for the pterin salvage pathway.

When in the above examples, other dihydrofolate reductase inhibitors replace methotrexate, e.g. aminopterin or 10-propargyl-5,8-dideazafolate or 2,4-diamino,5-(3',4'-dichlorophenyl),6-methylpyrimidine trimetrexate, or pyrimethamine or trimethorprim or pyritrexim 5,10-dideazatetrahydrofolate or 10-ethyl,10-deazaaminopterin, similar results of pterin salvage pathway blocking are obtained.

When other pressor agents are substituted for phenylephrine in Example XI, e.g., angiotensin II, norepinephrine or thromboxane analogs (i.e., u46619) similar results are obtained to those obtained in Example XI.

EXAMPLE XIII

Over time DAHP depletes tetrahydrobiopterin in the brain but more slowly than in the periphery (i.e., outside the brain). This example is directed to ameliorating effects of any tetrahydrobiopterin depletion in the brain in the course of the inventions herein.

Groups of Sprague-Dawley rats (6–10 per group) are injected intraperitoneally with a bolus of levodopa (20 mg/kg) and L-5-hydroxytryptophane (10 mg/kg) in saline.

The groups of rats are immediately thereafter injected i.p. with DAHP (1 g/kg) in the one case and with MTX (10 mg/kg) in another case and with LPS (15 mg/kg) in both cases.

After 12 hours, the animals are anesthetized with ether and blood nitrate levels are reduced more than 50%.

Another group of rats is given LPS (15 mg/kg) only.

Another group of rats is given MTX (10 mg/kg) and LPS (15 mg/kg) only.

Another group of rats is given DAHP (1 g/kg) and LPS (15 mg/kg) only.

In the cases where MTX and DAHP are injected, nitric oxide levels are reduced more than 50% compared to where LPS is given alone, significantly reducing the fall in blood pressure from LPS administration.

In the cases where levodopa and L-5-hydroxytryptophane are administered, symptoms resulting from catecholamine and serotonin depletion are significantly attenuated.

In another case the levodopa is administered at 5 mg/kg together with carbidopa (at a weight ratio of levodopa:carbidopa of 10:1). Similar results of reduction of symptoms resulting from catecholamine and serotonin depletion are obtained.

In another case, the LPS is administered one hour before the levodopa and L-5-hydroxytryptophane instead of concurrently with the DAHP and MTX. There is somewhat less of a reduction in fall in blood pressure compared to concurrent administration but still a significant improvement compared to where LPS is administered alone.

In still another case, the LPS is administered 3 hours before the levodopa and L-5-hydroxytryptophane instead of concurrently with the DAHP and MTX and the DAHP and MTX are administered alone and together with 20 mg/kg of $N^G$-methyl-L-arginine and in another case the $N^G$-methyl-L-arginine is administered without DAHP and MTX. For the case where MTX and DAHP are administered together with $N^G$-methyl-L-arginine, there is a significant improvement in reducing the fall in blood pressure from the LPS administration compared to where $N^G$-methyl-L-arginine is administered without DAHP or MTX and compared to where DAHP and MTX are administered without $N^G$-methyl-L-arginine and there are no deaths.

EXAMPLE XIV

A human is continuously administered interleukin-2 (10× $10^6$ units) for 5 days. Levodopa and L-5-hydroxytryptophane are respectively administered by continuous infusion all during this period at respective levels of 20 mg/kg/day and 10 mg/kg/day. DAHP (1 g/kg/day) or MTX (10 mg/kg/day) is administered by continuous infusion. The severe hypotension and vascular leak characteristic of the end of interleukin-2 therapy are significantly reduced. Neurological symptoms are mild.

EXAMPLE XV

Pithed Sprague-Dawly rats are injected intraperitoneally first with levodopa (20 mg/kg) and L-5-hydroxytryptophane (10 mg/kg) and then with LPS (15 mg/kg) alone or together with DAHP (300 mg/kg). After 3 hours LPS causes a dramatic fall in blood pressure but less so in animals given DAHP. At this time, a bolus injection of phenylephrine (6 μg/kg) is able to elicit a significant pressor response in animals treated with DAHP but less of a pressor response in animals not treated with DAHP. The injection of DAHP and phenylephrine significantly overcomes the fall in blood pressure caused by LPS administration.

EXAMPLE XVI

Sprague-Dawley rats are injected with 25 cc air subdermally in the dorsal area in accordance with the air pouch inflammatory model (Selye, H., Proc. Soc. Exper. Biol. and Med., 82, 328–333 (1953)). Into the air pouch formed, an inflammatory stimulus, croton oil (0.5% in 0.5 ml corn oil), is injected. Simultaneously, the rats in one group are administered i.p. DAHP (0.3 g/kg) plus MTX (5 mg/kg) and this administration is repeated every 12 hours for 5 days. The rats administered DAHP plus MTX are also administered i.p. with levodopa (20 mg/kg/day) and L-5-hydroxytryptophane (20 mg/kg/day). At the end of the 5 days, the group of rats given DAHP and MTX have significantly less nitrite in the fluid exudate contained in the granulominous lesion, less nitric oxide synthase activity in a homogenate of the granulominous tissue and less inflammation than the rats in the other group. Neuorological symptoms are mild.

In another case, the DAHP, MTX, levodopa and L-5-hydroxytryptophane are injected i.p. with the same daily doses except starting 2 days after the injection of air and croton oil. The inflammation is significantly improved at the end of 5 days, but not as much as in the case where DAHP plus MTX is given starting at the time of injection of air and croton oil.

Many variations of the above will be obvious to those skilled in the art. Thus, the invention is defined by claims.

What is claimed is:

1. A method of prophylaxis or treatment of a mammalian subject for chronic inflammation caused by induced nitric oxide production from arginine in immune cells, said method comprising administering to a mammalian subject susceptible to developing such inflammation selected from the group consisting of those at risk for allograft rejection, or administering to a mammalian subject having such inflammation, a therapeutically effective amount of at least one guanosine triphosphate pathway tetrahydrobiopterin synthesis antagonist which is not a substrate for tetrahydrobiopterin synthesis via the pterin salvage pathway, said guanosine triphosphate pathway tetrahydrobiopterin synthesis antagonist being the selected from the group consisting of (a) guanosine triphosphate cyclohydrolase I inhibitors except for 2,4-diamino-6-hydroxypyrimidine and (b) sepiapterin reductase inhibitors, said prophylaxis being carried out on said subject susceptible to developing such inflammation selected from the group consisting of those at risk for allograft rejection, said treatment being carried out on said subject having such inflammation.

2. A method of prophylaxis or treatment of a mammalian subject for chronic inflammation caused by induced nitric oxide production from arginine in immune cells, said method comprising administering to a mammalian subject susceptible to developing such inflammation selected from the group consisting of those at risk for allograft rejection, or administering to a mammalian subject having such inflammation, a therapeutically effective amount of at least one dihydrofolate reductase inhibitor and also administering to said subjects a catecholamine replacing non-toxic amount of levodopa with or without carbidopa and a serotonin replacing non-toxic amount of L-5-hydroxytryptophane, said prophylaxis being carried out on said subject susceptible to developing such inflammation selected from the group consisting of those at risk for allograft rejection, said treatment being carried out on said subject having such inflammation.

3. A method for the prophylaxis or treatment of a mammalian subject for chronic inflammation caused by induced nitric oxide production from arginine in immune cells, said method comprising administering to a mammalian subject susceptible to developing such inflammation selected from the group consisting of those at risk for allograft rejection, or administering to a mammalian subject having such inflammation, therapeutically effective amounts of at least one guanosine triphosphate pathway tetrahydrobiopterin synthesis antagonist which is a reduced pterin that is a substrate for tetrahydrobiopterin synthesis via the pterin salvage pathway and at least one dihydrofolate reductase inhibitor, said prophylaxis being carried out on said subject susceptible to developing such inflammation selected from the group consisting of those at risk for allograft rejection, said treatment being carried out on said subject having such inflammation.

4. The method of claim 3 which additionally comprises administering to said subject of a catecholamine replacing non-toxic amount of levodopa with carbidopa and a serotonin replacing non-toxic amount of L-5-hydroxytryptophane.

5. The method of claim 1 which additionally comprises administering to said subject of a catecholamine replacing non-toxic amount of levodopa with carbidopa and a serotonin replacing non-toxic amount of L-5-hydroxytryptophane.

6. The method of claim 1 which additionally comprises administering to said subject of a catecholamine replacing non-toxic amount of levodopa without carbidopa and a serotonin replacing non-toxic amount of L-5-hydroxytryptophane.

7. A method of prophylaxis or treatment of a mammalian subject for chronic inflammation caused by induced nitric oxide production from arginine in immune cells, said method comprising administering to a mammalian subject susceptible to developing such inflammation selected from the group consisting of those at risk for allograft rejection, or administering to a mammalian subject having such inflammation, therapeutically effective amounts of (a) at least one guanosine triphosphate pathway tetrahydrobiopterin synthesis antagonist which is not a substrate for tetrahydrobiopterin synthesis via the pterin salvage pathway, said guanosine triphosphate pathway tetrahydrobiopterin synthesis antagonist being selected from the group consisting of (i) guanosine triphosphate cyclohydrolase I inhibitors except for 2,4-diamino-6-hydroxypyrimidine and (ii) sepiapterin reductase inhibitors, and (b) at least one dihydrofolate reductase inhibitor, said prophylaxis being carried out on said subject susceptible to developing such inflammation selected from the group consisting of those at risk for allograft rejection, said treatment being carried out on said subject having such inflammation.

8. The method of claim 7 which additionally comprises administering to said subject of a catecholamine replacing non-toxic amount of levodopa with carbidopa and a serotonin replacing non-toxic amount of L-5-hydroxytryptophane.

9. The method of claim 7 which additionally comprises administering to said subject of a catecholamine replacing non-toxic amount of levodopa without carbidopa and a serotonin replacing non-toxic amount of L-5-hydroxytryptophane.

10. The method of claim 3 which additionally comprises administering to said subject of a catecholamine replacing non-toxic amount of levodopa without carbidopa and a serotonin replacing non-toxic amount of L-5-hydroxytryptophane.

11. The method of claim 1 wherein the guanosine triphosphate pathway tetrahydrobiopterin synthesis antagonist is a reduced pterin that is not a substrate for the pterin salvage pathway or is an oxidized pterin.

12. The method of claim 1 wherein the guanosine triphosphate pathway tetrahydrobiopterin synthesis antagonist is a sepiapterin reductase inhibitor.

13. The method of claim 12 wherein the sepiapterin reductase inhibitor is N-acetylserotonin.

14. The method of claim 3 wherein the guanosine triphosphate pathway tetrahydrobiopterin synthesis antagonist is selected from the group consisting of 7,8-dihydro-L-biopterin and L-sepiapterin.

15. The method of claim 7 wherein the guanosine triphosphate pathway tetrahydrobiopterin synthesis antagonist is a reduced pterin that is not a substrate for the pterin salvage pathway or is an oxidized pterin.

16. The method of claim 7 wherein the guanosine triphosphate pathway tetrahydrobiopterin synthesis antagonist is a sepiapterin reductase inhibitor.

17. The method of claim 16 wherein the sepiapterin reductase inhibitor is N-acetylserotonin.

18. A method of prophylaxis or treatment of a mammalian subject for inflammation caused by induced nitric oxide production from arginine in immune cells, said method comprising administering to a mammalian subject susceptible to developing such inflammation selected from the group consisting of those at risk for allograft rejection, or administering to a mammalian subject having such inflammation, therapeutically effective amount(s) of inhibitor of the synthesis of tetrahydrobiopterin in immune cells and also administering to said subjects a catecholamine replacing non-toxic amount of levodopa with or without carbidopa and a serotonin replacing non-toxic amount of L-5-hydroxytryptophane, said prophylaxis being carried out on said subject susceptible to developing such inflammation selected from the group consisting of those at risk for allograft rejection, said treatment being carried out on said subject having such inflammation.

* * * * *

UNITED STATES PATENT AND TRADEMARK OFFICE
CERTIFICATE OF CORRECTION

PATENT NO. : 5,877,176
DATED : March 02, 1999
INVENTOR(S) : Steven S. Gross

It is certified that error appears in the above-identified patent and that said Letters Patent is hereby corrected as shown below:

On the title page under "OTHER PUBLICATIONS", add --Hughes, S. R., et al, European Journal of Pharmacology, 191, 481-484 (1990).--

Signed and Sealed this

Sixteenth Day of November, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

| | |
|---|---|
| PATENT NO. | : 5,877,176 |
| APPLICATION NO. | : 08/151889 |
| DATED | : March 2, 1999 |
| INVENTOR(S) | : Steven S. Gross |

It is certified that error appears in the above-identified patent and that said Letters Patent is hereby corrected as shown below:

In column 1, lines 11-13, replace:

"This invention was made at least in part with Government support under Grants HL46403 from the National Institutes of Health."

with:

-- This invention was made with Government support under Contract Numbers HL46403 and HL34215 from the National Institutes of Health --.

Signed and Sealed this

Twenty-third Day of September, 2008

JON W. DUDAS
*Director of the United States Patent and Trademark Office*